United States Patent [19]
Heyboer

[11] 3,963,775
[45] June 15, 1976

[54] PROCESS FOR THE PRODUCTION OF 3-OXOGLUTARIC ACID
[75] Inventor: Nico Heyboer, Dieren, Netherlands
[73] Assignee: Akzona Incorporated, Asheville, N.C.
[22] Filed: Feb. 26, 1974
[21] Appl. No.: 445,941

[30] Foreign Application Priority Data
Mar. 1, 1973  Netherlands.................... 7302863

[52] U.S. Cl. ..................... 260/535 P; 260/465.4; 260/483; 260/484 P; 260/537 R; 260/544 K
[51] Int. Cl.² ........................................ C07C 59/12
[58] Field of Search..................... 260/535 P, 537 R

[56] References Cited
UNITED STATES PATENTS
3,773,821  11/1973  Broussard .................... 210/484 R
3,798,266  3/1974  Bottaccio et al. ............. 260/535 P FOREIGN PATENTS OR APPLICATIONS
7,112,249  3/1969  Netherlands ................... 260/535 R Primary Examiner—Paul J. Killos
Attorney, Agent, or Firm—Stevens, Davis, Miller & Mosher

[57] ABSTRACT

A feasible process for the production of 3-oxoglutaric acid is disclosed wherein ketene and phosgene are reacted in a molar ratio of ketene to phosgene of less than 2 in an organic solvent possessing a dielectric constant at 20°C between 2 and 22 and reacting the resulting product with a Zerewitinoff active hydrogen compound.

A method for the production of citric acid is also disclosed wherein ketene and phosgene are reacted in a molar ratio of the former to the latter of less than 2 in an organic solvent having a dielectric constant of from 2 to 22 at 20°C, reacting the resulting product with an aliphatic alcohol having 1 to 4 carbon atoms to form an acetone dicarboxylic dialkyl ester which in turn is subjected to a cyanohydrin synthesis. The cyanohydrin is then hydrolyzed to form citric acid which is then isolated.

10 Claims, No Drawings

PROCESS FOR THE PRODUCTION OF 3-OXOGLUTARIC ACID

The invention relates to a process for the preparation of acetone dicarboxylic acid (3-oxoglutaric acid) and derivatives thereof, by reacting ketene with phosgene in an organic solvent having a dielectric constant between 2 and 22, measured at 20°C, followed by reacting the resulting product with a compound containing an active hydrogen atom according to Zerewitinoff and isolation of the acetone dicarboxylic acid or derivative.

It is highly surprising to find that acetone dicarboxylic acid or derivatives thereof can be prepared by reacting ketene with phosgene by the present process, because HoubenWeyl, *Methoden der organischen Chemie, part 7/4*, p. 205, Georg Thieme, Stuttgart (1968) states that ketene cannot be brought into reaction with phosgene. In *Collection Czechoslov. Chem. Commun.*, Vol 20, (1955), p. 593, it is stated that ketene will react only with acid chlorides derived from relatively strong acids. One might therefor presume that the acid chloride (phosgene), which may be considered to have been derived from a weak acid (carbonic acid), will not react with ketene.

Recently, it has been ascertained that under certain conditions ketene and phosgene can be brought into reaction with each other, resulting in the formation of what is referred to as acetone dicarboxylic acid chloride. It is then necessary to use excess ketene and to have the reaction components dissolved in organic esters or ethers, or non-halogenated aromatic hydrocarbons having a dielectric constant of 2 to 8 measured at room temperature. This is disclosed in the Netherlands Patent Specification No. 7,112,249. A disadvantage of this method is that the large excess of the ketene used will result in a yield of acetone dicarboxylic acid or a derivative thereof of not more than 29%, based on ketene, and not more than 58%, based on phosgene (see the Example of the aforementioned Netherlands Patent Specification). It has now been found that in the reaction between ketene and phosgene, primarily 1 mole of phosgene reacts with 3 moles of ketene to form 1 mole of acetyl chloride and 1 mole of a presumably cyclic molecule which may be considered to be made up of 2 moles of ketene and 1 mole of phosgene minus 1 mole of hydrochloric acid. From said cyclic compound (hereinafter referred to as the precursor), the acetone dicarboxylic acid or derivative thereof is formed. It has also been found that no acetone dicarboxylic acid chloride is formed. The use of excess ketene according to the known method will cause the precursor readily to react further with the excess ketene and will lead to a considerable decrease in the yield of acetone dicarboxylic acid or the derivative thereof. In that case diketene and tarlike polymeric products are also formed from the ketene.

Moreover, according to the known method, it is preferred to use very pure ketene; in this connection, applicant has found that the use in the known process of less pure ketene will lead to the formation of more by-product and tar while the acetone dicarboxylic acid or derivative thereof will be obtained in a lower yield, based on ketene or phosgene. Besides, the larger amount of by-product generally makes it necessary in many instances for the finally obtained acetone dicarboxylic acid ester to be purified further by distillation.

The process according to the invention has the advantage that the acetone dicarboxylic acid or derivative thereof can be prepared in a high yield, based on ketene and phosgene and normally without the need for an additional purification of the acetone dicarboxylic acid alkyl ester. A further advantage is that a less carefully purified ketene may be used as starting material, e.g., ketene prepared on an industrial scale by thermolysis of acetic acid or acetone.

The process according to the present invention is characterized in that the molar ratio between the total amount of ketene added and the total amount of phosgene is less than 2.

The invention also relates to a process for the preparation of citric acid or a citrate, wherein an acetone dicarboxylic acid dialkyl ester is prepared by bringing ketene into reaction with phosgene in an organic solvent having a dielectric constant between 2 and 22 measured at 20°C, the molar ratio between the total amount of ketene added and the total amount of phosgene being smaller than 2, followed by reacting the resulting product with an aliphatic alcohol having 1 to 4 carbon atoms, after which the resulting acetone dicarboxylic acid dialkyl ester is subjected to a cyanohydrin synthesis; the cyanohydrin obtained is hydrolyzed and the resulting citric acid is isolated as such or as citrate. This non-fermentative process for the preparation of citric acid or salts thereof may be applied advantageously on an industrial scale because use may be made of an inexpensive starting material. At present, the preparation of citric acid on an industrial scale is usually carried out microbiologically by fermentation of carbohydrates, such as molasses.

In the reaction between ketene and phosgene the molar ratio between the total amount of ketene added and the total amount of phosgene is less than 2, and preferably not more than 1.4; the molar ratio is, for instance, between 1.4 and 0.06, more particularly between 1.3 and 0.15. Ketene to phosgene ratios lower than 0.06 are permissible but generally offer no additional advantages.

The reaction between ketene and phosgene generally takes place in an organic solvent having a dielectric constant between 2 and 22, preferably between 4 and 20, measured at 20°C. At 20°C, phosgene has a dielectric constant of approximately 4.3, so that liquid phosgene may be employed as the solvent used in the instant process; in that case, no other solvent is required. However, in addition to phosgene, it is preferred to employ a second solvent. Examples of suitable second solvents are diethyl ether, tetrahydrofuran, chloroform, dioxane, 1,2-dimethoxyethane, diethylene glycol dimethyl ether, methylene chloride, 1,2-dichloroethane, methyl acetate, methyl propionate, methyl butyrate, dimethyl malonate, ethyl acetate, isobutyl acetate, acetone, methylisobutyl ketone, and mixtures thereof.

Small amounts of a different solvent, such as n-hexane may be added, provided that the dielectric constant measured at 20°C of the solvent mixture is between the afore-mentioned limits of 2 and 22.

The temperature at which the reaction between ketene and phosgene is carried out will generally be between −30° and +50°C, preferably between −10° and + 30°C.

The pressure is not critical as long as the reaction takes place in the liquid phase. The reaction is usually carried out under autogeneous pressure, but higher or lower pressures may also be applied.

The reaction between the phosgene and the ketene may take place continuously, semi-continuously or discontinuously, for instance by the simultaneous addition of ketene and phosgene to an organic solvent, by adding ketene to a solution of phosgene in an organic solvent or by mixing separate solutions of ketene and phosgene in an organic solvent.

As mentioned supra, it has been found that the reaction between phosgene and ketene according to the invention results in the formation of acetyl chloride. This acetyl chloride may be obtained in a simple manner, for instance by distillation, and may be re-converted into ketene, for intance through acetic acid. It is also possible for the acetyl chloride to be marketed as such. Thus, the amount of ketene used as a starting material may be converted almost entirely into a commercial product. Based on this finding, the process according to the invention is preferably so carried out that after the reaction between phosgene and ketene has taken place, the excess phosgene and subsequently the acetyl chloride as well as part of the organic solvent that may have been used can be and are removed from the reaction mixture, in the order of their respective boiling points. The presence of ketene in the reaction mixture can no longer be detected. The boiling points of phosgene and acetyl chloride are +8°C and +51°C, respectively, so that these compounds may readily be separated by distillation. Distillation is preferably carried out under reduced pressure, in such a way that the temperature of the contents of the distillation vessel will generally be lower than about 25°C, and preferably lower than about 5°C.

The acetone dicarboxylic acid or derivatives thereof are obtained by bringing the precursor formed in the reaction between ketene and phosgene into reaction with a compound having an active hydrogen atom according to Zerewitinoff, examples thereof being water, ammonia; primary or secondary amines, such as methylamine, dimethylamine, dibutylamine, morpholine, piperazine, pyrazine and aniline; phenols such as cresol, α-napththol, hydroquinone, sulphur compounds, such as mercaptans e.g., methyl mercaptan, ethyl mercaptan, and lauryl mercaptan; and alcohols, such as methanol, ethanol, propanol, butanol, decanol, glycerol and pentaerythritol. The most desirable conditions under which the precursor is brought into reaction with the compounds having a Zerewitinoff active hydrogen atom can be simply established in a few experiments. It will often be the practice to bring a solution or dispersion of the precursor in an organic solvent into contact with one or more compounds having an active hydrogen atom at a temperature generally ranging between —30° and +150°C, and preferably between 0° and 90°C.

For the preparation of citric acid by the process according to the invention the precursor is preferably reacted with an aliphatic alcohol having 1 to 4 carbon atoms, such as methanol, ethanol and butanol. The reaction may be effected by any suitable method, but in practice it will generally be so carried out that in a preliminary treatment phosgene, acetyl chloride and optionally, the solvent used, are removed from the reaction mixture, for instance by distillation, followed by contacting the residue with the alcohol to be used.

The acetone dicarboxylic acid dialkyl ester obtained by the process according to the invention is then subjected to a cyanohydrin synthesis, which is known in itself and in which to the keto group is coupled to form a

—C(OH)CN group (see, for instance, Weygand-Hilgetag, Organische-Chemische Experimentierkunst, Barth, Leipzig, ed, 3rd(1964) p. 832) and German Patent Specification No. 562 390.

The reaction may be carried out with the use of a cyanide such as sodium cyanide or potassium cyanide in the presence of, e.g., hydrochloric acid, which may be introduced in the gaseous state or in the form of an aqueous solution, or with the aid of liquid hydrocyanic acid. The cyanide is generally used in an amount of approximately 1 to about 1.2 moles per mole of the dialkyl ester or hydrocyanic acid in an amount less than 1 mole per mole of the dialkyl ester.

The reaction generally takes place in an aqueous medium or in an organic dispersant such as methanol, 1,2-dichloroethane, diethyl ether or xylene. The reaction temperature will generally be in the range of 0° to 100°C, but preferably between 10° and 60°C.

The resulting cyanohydrin compound, which may have been isolated and purified, is then subjected to hydrolysis, wherein the two ester groups and the cyano group are converted in at least one step into free carboxyl groups or into a salt form thereof. The hydrolysis may be carried out in a known manner, for instance in an aqueous medium in the presence of a catalyst, such as sulphuric acid or hydrochloric acid, and at a temperature which will generally be between 10° and 150°C. (See U.S. Pat. No. 2,229,897 and the French Patent Specification No. 655,579).

It is known that citric acid is used in the manufacture of candies as an acidulent to enhance the flavor thereof while 3-oxoglutaric acid is useful as a starting material for various chemical synteses. Thus 3-oxoglutaric acid can be employed for the production of tropinone, and a dialkyl ester of 3-oxoglutaric acid can be used for the production of 2,4-dihydroxy-6-methylisophtalic acid-dialkyl-ester or of 1,3,5-pentanetriol.

EXAMPLE 1

To 150 ml of ethyl acetate are simultaneously added, with stirring, 13.5 g of gaseous ketene and 67.0 g of gaseous phosgene over a period of 3 hours at 0°C.

The reaction mixture is stirred for 2 hours, during which period the temperature is kept at 0°C, after which 50 ml of ethanol are added while maintaining the temperature at about 0°C. After evaporation of the resulting reaction mixture and distillation of the residue under reduced pressure, there are obtained 13.5 g of acetone dicarboxylic acid diethylester.

EXAMPLE 2

To 50 ml of liquid phosgene are added, with stirring, 5.4 g of gaseous ketene over a period of 2 hours at 0°C. The reaction mixture is stirred for 2 more hours at 0°C, after 70 ml of ethanol are added, while maintaining the temperature at about 10°C. After evaporation of the resulting solution and distillation of the residue under reduced pressure the yield is 4.5 g of acetone dicarboxylic acid diethylester.

EXAMPLES 3–14

To a mixture of an organic solvent and phosgene is added gaseous ketene at 0°C, with stirring, over a period of 15 to 65 minutes.

Stirring is continued for some time, after which the reaction mixture is poured into excess methanol whose temperature may rise to the boiling point. The mixture thus obtained is evaporated under reduced pressure at a temperature between 30° and 50°C, after which the amount of acetone dicarboxylic acid dimethyl ester present in the residue is determined gaschromatographically. Without having been additionally purified the resulting residue has a very high ester content, which is often about 95%. The resulting amount of pure dimethyl ester expressed as a percentage of the initial amount of ketene is given in the table below, along with the amounts of phosgene and ketene, the composition and the amount or organic solvent, the time for adding the ketene, and the total reaction time.

TABLE

| Examples | Amount of phosgene (g) | Amount of ketene (g) | Organic solvent Composition | Amount (ml) | Adding Time (min.) | Total Reaction time (min.) | Amount of dimethyl-ester (%) |
|---|---|---|---|---|---|---|---|
| 3 | 42.3 | 2.9 | methylacetate | 75 | 15 | 25 | 47 |
| 4 | 10.1 | 4.1 | " | 15 | 30 | 90 | 53 |
| 5 | 24.4 | 7.0 | " | 35 | 65 | 100 | 62 |
| 6 | 19.8 | 6.5 | " | 30 | 60 | 120 | 55 |
| 7 | 61.9 | 16.4 | n-butyl acetate | 50 | 60 | 75 | 56 |
| 8 | 36.6 | 9.1 | dimethyl malonate | 50 | 60 | 75 | 57 |
| 9 | 33.1 | 8.7 | tetrahydrofuran | 50 | 60 | 75 | 49 |
| 10 | 34.8 | 7.4 | dioxan | 50 | 60 | 75 | 57 |
| 11 | 37.7 | 9.2 | 1,2-dimethoxyethane | 50 | 60 | 70 | 63[1] |
| 12 | 33.8 | 8.2 | diethylene glycol dimethylether | 50 | 30 | 45 | 57 |
| 13 | 34.2 | 7.1 | methylisobutyl ketone | 50 | 60 | 75 | 48 |
| 14 | 22.9 | 6.5 | mixture of acetone and methyl acetate | 8 | 60 | 80 | 58 |

[1]Prior to the reaction mixture being poured into methanol, the volatile components, viz.: all of the phosgene, all of the acetyl chloride and part of the organic solvent were removed from the reaction mixture in vacuo and collected in a reservoir having a temperature of −80°C. In the reservoir were collected 30.5 g of phosgene, 5.4 g of acetyl chloride and 25.2 g of the organic solvent. It follows therefrom that 96% of the phosgene which has reacted has been converted into the acetone dicarboxylic acid ester. Moreover, it appears that about 94% of the ketene added has been converted into the acetone dicarboxylic acid ester and into the acetyl chloride.

1) Prior to the reaction mixture being poured into methanol, the volatile components, viz.: all of the phosgene, all of the acetyl chloride and part of the organic solvent were removed from the reaction mixture in vacuo and collected in a reservoir having a temperature of −80°C. In the reservoir were collected 30.5 g of phosgene, 5.4 g of acetyl chloride and 25.2 g of the organic solvent. It follows therefrom that 96% of the phosgene which has reacted has been converted into the acetone dicarboxylic acid ester. Moreover, it appears that about 94% of the ketene added has been converted into the acetone dicarboxylic acid ester and into the acetyl chloride.

EXAMPLE 15

To a mixture of 174 g of acetone dicarboxylic acid and 50 mg of sodium cyanide are added, over a period of 1 hour, 90 ml of liquid prussic acid at −10°C, with stirring and cooling to 35°C. After the mixture has been stirred for another hour at room temperature 1 ml of 96%-sulphuric acid is added and the excess prussic acid is removed in vacuo. To the crystallized cyanohydrin are added 750 ml of 4 N hydrochloric acid. After 16 hours' stirring at room temperature, at which the cyanohydrin goes into solution, the solution is boiled with refluxing over a period of 7 hours. From the solution pure citric acid is obtained in a 91% yield.

What is claimed is:

1. A process for the preparation of 3-oxoglutaric acid and derivatives comprising
    a. reacting ketene with phosgene in an organic solvent having a dielectric constant between 2 and 22 measured at 20°C,
    b. reacting the product of (a) with a compound containing an active hydrogen atom according to Zerewitinoff, and
    c. isolating the resulting product, with the proviso that the molar ratio between the total amount of ketene and the total amount of phosgene is less than 2.
2. The process of claim 1 wherein the molar ratio is between 0.66 and 1.4.
3. The process of claim 1 wherein ketene is reacted with phosgene at a temperature between −30° and +50°C.
4. The process of claim 1 wherein said organic solvent has a dielectric constant between 4 and 20.
5. The process of claim 1 wherein acetyl chloride, which forms during the reaction between ketene and phosgene, is removed from the reaction mixture.
6. The process of claim 1 wherein said compound containing an active hydrogen atom according to Zerewitinoff is water.
7. The process of claim 1 wherein said compound containing an active hydrogen atom according to Zerewitinoff is an alcohol.
8. The process of claim 7 wherein said alcohol is an aliphatic alcohol containing 1 to 4 carbon atoms.
9. A process which comprises reacting ketene and phosgene in an organic solvent having a dielectric constant between 2 and 22 measured at 20°C while mixed in a molar ratio of ketene to phosgene of less than 2 to 1, reacting the resulting product with a compound containing an active hydrogen atom as determined by the Zerewitinoff method and isolating the resulting reaction product.
10. The process of claim 9 wherein the active hydrogen containing compound is water, ammonia, a primary or secondary amine, a phenol, a mercaptan or an alcohol.

* * * * *